US 6,540,933 B1

(12) United States Patent
Sievert et al.

(10) Patent No.: US 6,540,933 B1
(45) Date of Patent: Apr. 1, 2003

(54) PROCESS FOR THE PRODUCTION OF HEXAFLUOROPROPYLENE FROM $CClF_2CClFCF_3$ AND AZEOTROPES OF $CClF_2CClFCF_3$ WITH HF

(75) Inventors: Allen Capron Sievert, Elkton, MD (US); V. N. Mallikarjuna Rao, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/701,449

(22) PCT Filed: Jun. 2, 1999

(86) PCT No.: PCT/US99/12286

§ 371 (c)(1),
(2), (4) Date: Nov. 27, 2000

(87) PCT Pub. No.: WO99/62849

PCT Pub. Date: Dec. 9, 1999

Related U.S. Application Data

(60) Provisional application No. 60/087,755, filed on Jun. 2, 1998.

(51) Int. Cl.[7] .......................... C09K 5/04; C07C 19/01; C07C 17/20
(52) U.S. Cl. .......................... 252/67; 570/134; 570/136
(58) Field of Search .......................... 252/67; 570/136, 570/134

(56) References Cited

U.S. PATENT DOCUMENTS

| 2,576,823 A | 11/1951 | Benning |
| 5,043,491 A | 8/1991 | Webster et al. |
| 5,057,634 A | 10/1991 | Webster et al. |
| 5,068,472 A | 11/1991 | Webster et al. |
| 5,264,639 A | * 11/1993 | Morikawa et al. .......... 570/168 |
| 5,523,501 A | 6/1996 | Kellner et al. |
| 5,573,654 A | 11/1996 | Cheurkov et al. |
| 6,329,559 B1 | 12/2001 | Sievert et al. |

FOREIGN PATENT DOCUMENTS

| DE | 1237084 | 3/1967 |
| EP | 002098 | 5/1979 |
| EP | 0 434407 A | 6/1991 |
| EP | 0 434409 A | 6/1991 |
| GB | 821 211 A | 10/1959 |
| GB | 902590 | 8/1962 |
| GB | 938070 A | 9/1963 |
| GB | 313118 A | 11/1997 |
| GB | 2313118 A | 11/1997 |
| WO | WO 9008748 A | 8/1990 |
| WO | WO 9105752 A | 5/1991 |
| WO | WO 9719751 A | 6/1997 |
| WO | WO 99/62851 | 12/1999 |

OTHER PUBLICATIONS

J. Kricala et al., J. Fluorine, 43 (1989), pp. 155–175.

* cited by examiner

*Primary Examiner*—John Hardee

(57) ABSTRACT

A process for the manufacture of $CF_3CF=CF_2$ is disclosed. The process involves contacting 2,3-dichloro-1,1,1,2,3,3-hexafluoropropane with at least 0.1 mole of hydrogen in a reaction vessel of titanium, nickel or iron or their alloys, which is either empty or packed with particles or formed shapes of titanium, nickel or iron or their alloys, at a temperature within the range of from about 350° C. to about 600° C. and for a time sufficient to produce hexafluoropropene. Also disclosed are compositions which comprise hydrogen fluoride in combination with an effective amount of $CClF_2CClFCF_3$ to form an azeotrope or azeotrope-like composition with hydrogen fluoride. The compositions contain from about 8.7 to 33.6 mole percent $CClF_2CClFCF_3$.

13 Claims, No Drawings

PROCESS FOR THE PRODUCTION OF HEXAFLUOROPROPYLENE FROM $CClF_2CClFCF_3$ AND AZEOTROPES OF $CClF_2CClFCF_3$ WITH HF

This application represents a national filing under 35 USC 371 of International Application No. PCT/US99/12286 filed Jun. 2, 1999 and claims the priority benefit of U.S. Provisional Application No. 60/087,755 filed Jun. 2, 1998.

FIELD OF THE INVENTION

The present invention relates to the synthesis of hexafluoropropene from 2,3-dichloro-1,1,1,2,3,3-hexafluoropropane and the azeotrope of the latter compound with HF.

BACKGROUND

Commercial methods for the preparation of hexafluoropropene ($CF_3CF=CF_2$ or HFP), a fluoromonomer, typically involve temperatures greater than 600° C. The high reaction temperatures lead to the formation of perfluoroisobutylene, an extremely toxic compound which is costly to remove and destroy (e.g., see European Patent Application No. 002,098). Processes for the manufacture of HFP at lower temperatures based on the use of acyclic three-carbon hydrocarbons or partially halogenated three-carbon hydrocarbons are disclosed in U.S. Pat. Nos. 5,043,491, 5,057,634 and 5,068,472.

There is a need for alternative methods of manufacturing hexafluoropropene.

2,3-Dichloro-1,1,1,2,3,3-hexafluoropropane (i.e., $CClF_2CClFCF_3$ or CFC-216ba) is a known compound. For example, it can be prepared as described in J. Kvicala et al., J. Fluorine Chem., 43 (1989) 155–175. $C_3Cl_2F_5$ containing 90% of $CF_3CClFCCl_2F$ (CFC-215bb) is reacted with a fluorination mixture containing HF (90 vol. %) and $Cl_2$ (10 vol. %) in the vapor phase in the presence of a ferric chloride on charcoal catalyst at 390° C. to obtain a $C_3Cl_2F_6$ product which contained 85% $CClF_2CClFCF_3$ and 15% $CF_3CCl_2CF_3$. The product was collected in an aqueous sodium hydroxide trap. A similar preparation is disclosed in German Patent Application No. DE 1,237,084. CFC-215bb is reacted in the vapor phase at 115° C. with an $HF/Cl_2$ mixture using an $SbCl_5$ supported on carbon catalyst which was treated with HF prior to use. The product gas mixture was washed with water and aqueous NaOH.

SUMMARY OF THE INVENTION

This invention provides a process for the manufacture of $CF_3CF=CF_2$. The process comprises contacting 2,3-dichloro-1,1,1,2,3,3-hexafluoropropane with at least 0.1 mole of hydrogen in a reaction vessel of titanium, nickel or iron or their alloys, which is either empty or packed with particles or formed shapes of titanium, nickel or iron or their alloys, at a temperature within the range of from about 350° C. to about 600° C. and for a time sufficient to produce hexafluoropropene.

Also provided are compositions which comprise hydrogen fluoride in combination with an effective amount of $CClF_2CClFCF_3$ to form an azeotrope or azeotrope-like composition with hydrogen fluoride, said composition containing from about 8.7 to 33.6 mole percent $CClF_2CClFCF_3$.

DETAILED DESCRIPTION

CFC-216ba or its azeotrope with HF (see below) can be dechlorinated with hydrogen to afford hexafluoropropylene. The reaction of CFC-216ba with hydrogen is done in a reaction vessel of titanium, nickel or iron or their alloys. A reaction vessel of these materials (e.g., a metal tube) optionally packed with the metal in suitable form may also be used. When reference is made to alloys, it is meant a nickel alloy containing from 1 to 99.9% (by weight) nickel, an iron alloy containing from 0.2 to 99.9% (by weight) iron and a titanium alloy containing 72 to 99.8% (by weight) titanium.

Most preferred for the practice of this invention is an empty reaction vessel made of nickel or alloys of nickel such as those containing 40% to 80% nickel, e.g., Inconel® 600 nickel alloy, Hastelloy® C617 nickel alloy or Hastelloy® C276 nickel alloy.

When used for packing the metal or alloys may be particles or formed shapes such as, perforated plates, saddles, rings, wire, screen, chips, pipe, shot, gauze and wool.

The reaction temperature can be between from about 350° C. to about 600° C. Preferably the reaction temperature is at least about 450° C.

The amount of hydrogen contained in the gas stream contacted with CFC-216ba should be at least 0.1 mole per mole of CFC-216ba. In general, the amount of hydrogen is between from about 0.2 to 60 moles per mole of CFC-216ba and more preferably is between from about of 0.4 to 10 moles per mole of CFC-216ba. The higher the ratio of $H_2$:CFC-216ba, the more $CHF_2CHFCF_3$ is formed. The hydrogen can be diluted with an inert gas, e.g., nitrogen, helium or argon.

Although substantial conversions can be achieved in a once-through system, recycle of unreacted CFC-216ba can be employed in a conventional manner.

In addition to the preparations described above, CFC-216ba may also be prepared by contacting CFC-215bb in the vapor phase (e.g., at 115° C.) with a mixture of HF and $Cl_2$ in the presence of a catalyst (e.g., an $SbCl_5$ supported on carbon catalyst which is treated with HF prior to use). The reaction product effluent comprises CFC-215bb, CFC-216ba, HF and HCl before scrubbing with water. As noted above, it has now been found that CFC-216ba forms an azeotrope with HF. A portion of the CFC-216ba produced can be used as an azeotropic composition of CFC-216ba with HF and reacted to form CFC-217ba (see below); with another portion of the CFC-216ba being used for HFP production.

The present invention further provides compositions which consist essentially of hydrogen fluoride and an effective amount of $CClF_2CClFCF_3$ to form an azeotropic combination with hydrogen fluoride. By effective amount is meant an amount which, when combined with HF, results in the formation of an azeotrope or azeotrope-like mixture. As recognized in the art, an azeotrope or an azeotrope-like composition is an admixture of two or more different components which, when in liquid form under given pressure, will boil at a substantially constant temperature, which temperature may be higher or lower than the boiling temperatures of the individual components, and which will provide a vapor composition essentially identical to the liquid composition undergoing boiling.

An azeotrope is a liquid mixture that exhibits a maximum or minimum boiling point relative to the boiling points of surrounding mixture compositions. An azeotrope is homogeneous if only one liquid phase is present. An azeotrope is heterogeneous if more than one liquid phase is present. Regardless, a characteristic of minimum boiling azeotropes is that the bulk liquid composition is then identical to the vapor composition in equilibrium therewith, and distillation of the azeotropic mixture is ineffective as a separation technique. For the purpose of this discussion, azeotrope-like composition means a composition which behaves like an azeotrope (i.e., has constant-boiling characteristics or a tendency not to fractionate upon boiling or evaporation). Thus, the composition of the vapor formed during boiling or evaporation of such compositions is the same as or substantially the same as the original liquid composition. Hence, during boiling or evaporation, the liquid composition, if it changes at all, changes only to a minimal or negligible extent. This is to be contrasted with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotropic composition may change when the azeotrope or azeotrope-like liquid composition is subjected to boiling at different pressures. Thus an azeotrope or an azeotrope-like composition may be defined in terms of the unique relationship that exists among components or in terms of the compositional ranges of the components or in terms of exact weight percentages of each component of the composition characterized by a fixed boiling point at a specified pressure. It is also recognized in the art that various azeotropic compositions (including their boiling points at particular pressures) may be calculated (see, e.g., W. Schotte, Ind. Eng. Chem. Process Des. Dev. 1980, 19, pp 432–439). Experimental identification of azeotropic compositions involving the same components may be used to confirm the accuracy of such calculations and/or to modify the calculations for azeotropic compositions at the same or other temperatures and pressures.

Compositions may be formed which consist essentially of azeotropic combinations of hydrogen fluoride with $CClF_2CClFCF_3$. These include a composition consisting essentially of from about 91.3 to about 66.4 mole percent HF and from about 8.7 to 33.6 mole percent $CClF_2CClFCF_3$ (which forms an azeotrope boiling at a temperature from between about −40° C. and about 120° C. and a pressure between about 9.5 kPa and about 2943 kPa).

At atmospheric pressure, the boiling points of hydrofluoric acid and CFC-216aa are about 19.5° C. and 32.6° C., respectively. At a pressure of 23.4 psia (161 kPa) and 20° C., the relative volatility was found to be nearly 1.0 as 84.6 mole percent HF and 15.4 mole percent CFC-216ba was approached. At a pressure of 805 kPa (117 psia) and 69.8° C., the relative volatility was found to be nearly 1.0 as 77.1 mole percent HF and 22.9 mole percent CFC-216ba was approached. These data indicate that the use of conventional distillation procedures will not result in the separation of a substantially pure compound because of the low value of relative volatility of the compounds.

To determine the relative volatility of HF with each of CFC-216ba, the so-called PTx Method was used. In this procedure, the total absolute pressure in a cell of known volume is measured at a constant temperature for various known binary compositions. Use of the PTx Method is described in greater detail in "Phase Equilibrium in Process Design", Wiley-Interscience Publisher, 1970, written by Harold R. Null, on pages 124 to 126, the entire disclosure of which is hereby incorporated by reference. Samples of the vapor and liquid, or vapor and each of the two liquid phases under those conditions where two liquid phases exist, were obtained and analyzed to verify their respective compositions.

These measurements can be reduced to equilibrium vapor and liquid compositions in the cell by an activity coefficient equation model, such as the Non-Random. Two-Liquid (NRTL) equation, to represent liquid phase non-idealities. Use of an activity coefficient equation, such as the NRTL equation, is described in greater detail in "The Properties of Gases and Liquids". 4th Edition, publisher McGraw Hill, written by Reid, Prausnitz and Poling, on pages 241 to 387; and in "Phase Equilibria in Chemical Engineering", published by Butterworth Publishers, 1985, written by Stanley M. Walas, pages 165 to 244; the entire disclosure of each of the previously identified references are hereby incorporated by reference.

Without wishing to be bound by any theory or explanation, it is believed that the NRTL equation can sufficiently predict whether or not mixtures of HF and CFC-216ba behave in an ideal manner, and can sufficiently predict the relative volatilities of the components in such mixtures. Thus, while HF has a good relative volatility compared to CFC-216ba at low CFC-216ba concentrations, the relative volatility becomes nearly 1.0 as 15.4 mole percent CFC-216ba was approached at 20° C. This would make it impossible to separate CFC-216ba from HF by conventional distillation from such a mixture. Where the relative volatility approaches 1.0 defines the system as forming a near-azeotrope. Where the relative volatility is 1.0 defines the system as forming an azeotrope.

It has been found that azeotropes of HF and CFC-216ba are formed at a variety of temperatures and pressures. At a pressure of 23.4 psia (161 kPa) and 20° C. the azeotrope vapor composition was found to be about 84.6 mole percent HF and about 15.4 mole percent CFC-216ba. At a pressure of 117 psia (805 kPa) and 69.8° C., the azeotrope vapor composition was found to be about 77.1 mole percent HF and about 22.9 mole percent CFC-216ba. Based upon the above findings, it has been calculated that an azeotropic composition of about 91.3 mole percent HF and about 8.7 mole percent CFC-216ba can be formed at −40° C. and 1.38 psia (9.5 kPa) and an azeotropic composition of about 66.4 mole percent HF and about 33.6 mole percent CFC-216ba can be formed at 120° C. and 427 psia (2943 kPa). Accordingly, the present invention provides an azeotrope or azeotrope-like composition consisting essentially of from about 91.3 to 66.4 mole percent HF and from about 8.7 to 33.6 mole percent CFC-216ba, said composition having a boiling point from about −40° C. at 9.5 kPa to about 120° C. at 2943 kPa. At all temperatures below 100° C., these azeotropes are considered to be heterogeneous in that two liquid phases are present. At 20° C., the calculated concentrations of the two liquid phases are about 5.2 and 98.7 mole % HF; at 69.8° C., the calculated liquid phase concentrations are 11.4 and 97.3 mole % HF.

The CFC-216ba/HF azeotrope is useful as recycle to a chlorofluorination reactor (e.g., the reactor used for chlorofluorinating CFC-215bb), where the recycled HF can function as a reactant and the recycled CFC-216ba can function to moderate the temperature effect of the heat of reaction. The azeotrope can also be use as a starting material for the production of 1,1,1,2,3,3-hexafluoropropene (i.e., $CF_3CF=CF_2$ or HFP), 2-chloro-1,1,1,2,3,3,3-heptafluoropropane (i.e., $CF_3CClFCF_3$ or CFC-217ba) and perfluoropropane (i.e., $CF_3CF_2CF_3$ or FC-218). It will also be apparent to one of ordinary skill in the art that distillation including azeotropes with HF can typically be run under more convenient conditions than distillation without HF (e.g., where HF is removed prior to distillation). HF may be removed from the halogenated hydrocarbon components of the product mixture using conventional aqueous solution scrubbing techniques. However, the production of substantial amounts of scrubbing discharge can create aqueous waste disposal concerns.

Without further elaboration, it is believed that one skilled in the art can, using the description herein, utilize the present invention to its fullest extent. The following embodiments are, therefore, to be construed as merely illustrative, and do not constrain the remainder of the disclosure in any way whatsoever.

EXAMPLES

LEGEND

216ba is $CClF_2CClFCF_3$

236ea is $CHF_2CHFCF_3$

HFP is $CF_3CF=CF_2$

General Procedure for Product Analysis

The following general procedure is illustrative of the method used. Part of the total reactor effluent was sampled on-line for organic product analysis using a Hewlett Packard HP 5890 gas chromatograph equipped with a 20' (6.1 m) long×⅛' (0.32 cm) diameter tubing containing Krytox® perfluorinated polyether on an inert carbon support. The helium flow was 35 mL/min. Gas chromatographic conditions were 70° C. for an initial hold period of three minutes followed by temperature programmning to 180° C. at a rate of 6° C./minute.

The bulk of the reactor effluent containing organic products and also inorganic acids such as HCl and HF was treated with aqueous caustic prior to disposal.

EXAMPLE 1

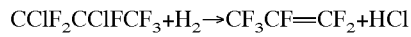

$CClF_2CClFCF_3+H_2 \rightarrow CF_3CF=CF_2+HCl$

Through a 6' (1.83 m)×¼' (6.4 mm) O.D. Inconel® 600 nickel alloy tubing maintained at 500° C. in a fluidized sand bath was sent a feed mixture of $CClF_2CClFCF_3$ (5 mL/hour, 0.060 mmol/minute) and hydrogen (50 sccm, $8.8 \times 10^{-7}$ m$^3$/s). The organic feed was first vaporized and mixed with hydrogen before admission to the reactor. The reaction was conducted at atmospheric pressure (0 psig, 101 kPa). Product analysis in area % indicated 18.7% HFP, 2.9% 236ea and 77.2% unconverted starting material (216ba) in addition to small quantities of other products.

The experiment was substantially repeated, except that the hydrogen flow rate was 20 sccm ($3.3 \times 10^{-7}$ m$^3$/s). Product analysis in area% indicated 14.5% HFP, 2.2% 236ea and 82.3 unconverted starting material (216ba) in addition to small quantities of other products.

What is claimed is:

1. A composition comprising:
    (a) hydrogen fluoride; in combination with
    (b) an effective amount of $CClF_2CClFCF_3$ to form an azeotrope or azeotrope-like composition with hydrogen fluoride;
    said composition containing from about 8.7 to 33.6 mole percent $CClF_2CClFCF_3$.

2. A composition consisting essentially of an azeotropic combination of hydrogen fluoride with 2,3-dichloro-1,1,1,2,3,3-hexafluoropropane.

3. THe method for preparing the azeotropic composition of claim 2, comprising;
    (a) contacting 2,3,3-trichloro-1,1,1,2,3-pentafluoropropane in the vapor phase with a mixture of HF and $Cl_2$ in the presence of a catalyst; and
    (b) using a portion of the 2,3-dichloro-1,1,1,2,3,3-hexafluoropropane produced to obtain said azeotropic composition.

4. The method of claim 3 wherein the composition obtained in (b) is recycled to the reactor used for the chlorofluorination (a).

5. The method of using the azeotropic composition prepared by claim 3, comprising:
    (1) reacting the composition obtained in (b) to form 2-chloro-1,1,1,2,3,3,3-heptafluoropropane; and
    (2) using another portion of the 2,3-dichloro-1,1,1,2,3,3-hexafluoropropane prepared for manufacturing hexafluoropropylene.

6. The method of claim 5 wherein the $CF_3CF=CF_2$, is manufactured by a process comprising contacting 2,3-dichloro-1,1,1,2,3,3-hexafluoropropane with at least 0.1 mole of hydrogen in a reaction vessel of titanium, nickel or iron or their alloys, which is either empty or packed with particles or formed shapes of titanium, nickel or iron or their alloys, at a temperature within the range of from about 350° C. to about 600° C. and for a time sufficient to produce hexafluoropropene.

7. The method of claim 3 further comprising contacting a portion of the 2,3-dichloro-1,1,1,2,3,3-hexafluoropropane obtained in (a) with 0.1 mole of hydrogen in a reaction vessel of titanium, nickel or iron or their alloys, which is either empty or packed with particles or formed shapes of titanium, nickel or iron or their alloys, at a temperature within the range of from about 350° C. to about 600° C. and for a time sufficient to produce hexafluoropropene.

8. The method for preparing the azeotropic composition of claim 1, comprising:
    (a) contacting 2,3,3-trichloro-1,1,1,2,3-pentafluoropropane in the vapor phase with a mixture of HF and $Cl_2$ in the presence of a catalyst; and
    (b) using a portion of the 2,3-dichloro-1,1,1,2,3,3-hexafluoropropane produced to obtain said azeotropic composition.

9. The method of claim 8 wherein the composition obtained in (b) is recycled to the reactor used for the chlorofluorination (a).

10. The method of using the azeotropic composition prepared by claim 8, comprising:
    (1) reacting the composition obtained in (b) to form 2-chloro-1,1,1,2,3,3,3-heptafluoropropane; and
    (2) using another portion of the 2,3-dichloro-1,1,1,2,3,3-heptafluoropropane prepared for manufacturing hexafluoropropylene.

11. The method of claim 10 wherein the $CF_3CF=CF_2$, is manufactured by a process comprising contacting 2,3-dichloro-1,1,1,2,3,3-hexafluoropropane with at least 0.1 mole of hydrogen in a reaction vessel of titanium, nickel or iron or their alloys, which is either empty or packed with particles or formed shapes of titanium, nickel or iron or their alloys, at a temperature within the range of from about 350° C. to about 600° C. and for a time sufficient to produce hexafluoropropene.

12. The method of claim 8 further comprising contacting a portion of the 2,3-dichloro-1,1,1,2,3,3-hexafluoropropane obtained in (a) with 0.1 mole of hydrogen in a reaction vessel of titanium, nickel or iron or their alloys, which is either empty or packed with particles or formed shapes of titanium, nickel or iron or their alloys, at a temperature within the range of from about 350° C. to about 600° C. and for a time sufficient to produce hexafluoropropene.

13. A process for the manufacture of $CF_3CF=CF_2$, comprising:

preparing 2,3-dichloro-1,1,1,2,3,3-hexafluoropropane by contacting $CF_3CClFCCl_2F$ in the vapor phase with a mixture of HF and $Cl_2$ in the presence of a catalyst;

using a portion of the $CClF_2CClFCF_3$ to form a composition consisting essentially of an azeotropic combination of hydrogen fluoride with 2,3-dichloro-1,1,1,2,3,3-hexafluoropropane; and contacting another portion of the $CClF_2CClFCF_3$ with at least 0.1 mole of hydrogen in a reaction vessel of titanium, nickel or iron or their alloys, which is either empty or packed with particles or formed shapes of titanium, nickel or iron or their alloys, at a temperature within the range of from about 350° C. to about 600° C. and for a time sufficient to produce hexafluoropropene.

\* \* \* \* \*